United States Patent
Najor

(10) Patent No.: US 6,392,550 B1
(45) Date of Patent: May 21, 2002

(54) METHOD AND APPARATUS FOR MONITORING DRIVER ALERTNESS

(75) Inventor: Rene A. Najor, Farmington Hills, MI (US)

(73) Assignee: Ford Global Technologies, Inc., Dearborn, MI (US)

( * ) Notice: Subject to any disclaimer, the term of this patent is extended or adjusted under 35 U.S.C. 154(b) by 54 days.

(21) Appl. No.: 09/716,000

(22) Filed: Nov. 17, 2000

(51) Int. Cl.⁷ .............................................. G08B 23/00
(52) U.S. Cl. ........................ 340/576; 340/575; 340/439; 340/665; 340/666; 340/667
(58) Field of Search ................................ 340/576, 575, 340/439, 665, 666, 667

(56) References Cited

U.S. PATENT DOCUMENTS

| | | |
|---|---|---|
| 3,903,514 A | 9/1975 | Mazzola |
| 4,177,460 A | 12/1979 | Hoinski et al. |
| 4,604,611 A | 8/1986 | Seko et al. |
| 5,474,327 A | 12/1995 | Schousek |
| 5,682,144 A | 10/1997 | Mannik |
| 5,689,241 A | 11/1997 | Clark, Sr. et al. |
| 5,691,693 A | * 11/1997 | Kithil ........................ 340/439 |
| 5,732,375 A | 3/1998 | Cashler |
| 5,798,695 A | * 8/1998 | Metalis et al. ............... 340/576 |
| 5,813,989 A | 9/1998 | Saitoh et al. |
| 5,975,568 A | 11/1999 | Speckhart et al. |
| 5,987,370 A | * 11/1999 | Murphy et al. .............. 340/665 |
| 5,990,795 A | * 11/1999 | Miller ......................... 340/576 |
| 6,016,103 A | 1/2000 | Leavitt |
| 6,070,115 A | 5/2000 | Oestreicher et al. |
| 6,107,922 A | 8/2000 | Bryuzgin |
| 6,158,768 A | * 12/2000 | Steffens, Jr. et al. ......... 340/562 |

* cited by examiner

Primary Examiner—Jeffrey Hofsass
Assistant Examiner—Hung Nguyen
(74) Attorney, Agent, or Firm—Gary A. Smith

(57) ABSTRACT

A system for determining the alertness of a driver of a vehicle by monitoring the driver's seated posture. A pressure sensor array disposed in or on the seat produces output signals that indicate the pattern of pressure exerted by the driver's body at a plurality of points distributed over the seat surface. A microprocessor-based alertness evaluation module receives pressure pattern data from the sensor array and uses neural network processing techniques to determine a probable driver alertness level based upon changes in the pattern of pressure. The sensor array may also be used to supply data to an occupant restraint system control module. Using the sensor for two purposes avoids the additional cost of providing a dedicated alertness sensor is avoided.

20 Claims, 1 Drawing Sheet

METHOD AND APPARATUS FOR MONITORING DRIVER ALERTNESS

FIELD OF THE INVENTION

This invention relates to a system for monitoring the degree of alertness of the driver of an automotive vehicle, and more particularly to such a system that utilizes the driver's seated posture to determine when the driver is becoming drowsy.

BACKGROUND OF THE INVENTION

A significant number of automobile accidents are caused by the driver of a vehicle being tired, drowsy, or otherwise insufficiently alert to safely operate the vehicle. Many methods have been proposed to detect signs that a driver is becoming drowsy and/or is not fully alert. Examples of such systems are those which detect the driver's head tipping or nodding forward, those which detect an increased blink rate or the eyes closing, and those which detect the accuracy with which the vehicle is tracking within the lane in which it is driving.

It is known to install a pressure sensing device in the driver and/or passenger seat of an automobile to monitor the amount and/or the distribution of pressure exerted on the seat by a person or object occupying the seat. In some proposed systems, the sensor detects pressure at a plurality of points distributed over the surface of the seat, and the resulting pressure pattern is fed to an occupant restraint system controller. The controller uses the data to suppress and/or adjust the deployment of occupant restraints such as airbags. For example, the controller is able to distinguish between the patterns indicating a heavy occupant, calling for a relatively rapid and/or high-powered inflation of the airbag; a lighter occupant, calling for a slower and lower-powered inflation; and a child safety seat, calling for complete suppression of bag deployment. Such a system, using variable resistors as pressure sensors, is taught by U.S. Pat. No. 5,474,327.

SUMMARY OF THE INVENTION

It is an objective of this invention to provide a method and apparatus for monitoring driver alertness that reliably and accurately determine when the driver's level of alertness has degraded to the point where the driver may not be able to operate the vehicle safely.

It is a further objective of this invention to provide a method and apparatus for monitoring driver alertness that utilizes a seat-mounted pressure sensor that may also provide occupant status information to an occupant restraint system controller.

In achieving these and other objectives, a preferred embodiment of the invention disclosed herein comprises a sensor array disposed in the driver's seat to sense a pattern of pressure exerted by the driver's body at a plurality of points distributed over the seat surface. The invention system further comprises a computer which receives pressure pattern data from the sensor array and determines a probable driver alertness level based upon changes in the pattern of pressure detected by the sensor array.

According to another feature of the invention, the sensor array may also be used to supply data to an occupant restraint system controller. For example, the sensor may provide information regarding the driver weight and seating position in order to allow the restraint controller to make restraint deployment decisions. Using the sensor for two purposes avoids the additional cost of providing a dedicated alertness sensor is avoided.

According to another feature of the invention, a method of monitoring the alertness of a driver is provided comprising the steps of measuring a first pressure pattern exerted by the driver on a plurality of points distributed over the seat surface at a first time, measuring a second pattern of pressure at a later time, and determining a probable driver alertness level based upon a comparison of the first and second patterns. According to a preferred embodiment of the invention disclosed herein, the sensor array comprises a plurality of variable resistors located in the seat bottom and the seat back. The sensor array detects pressure at a sufficient number of discrete points distributed over the seat surface to provide an indication of the driver's posture at any particular moment. The computer which receives the pressure pattern data from the sensor array utilizes a neural network processing technique which enables it to determine the probable driver alertness level based upon changes in the driver's posture over time. The alertness level determination may be based upon, for example, the assumption that a driver begins to slouch in the seat as he/she becomes tired and his/her alertness level decreases. Alternatively, the alertness level determination may be based upon variations in the rate at which the driver makes changes in his/her position in the seat. The neural network processing technique allows the system to "learn" a particular driver's normal or natural posture and or rate of position changes, and make determinations about how changes from these normal values occur as the driver's level of alertness change.

DETAILED DESCRIPTION OF THE PREFERRED EMBODIMENT

Figure 1:
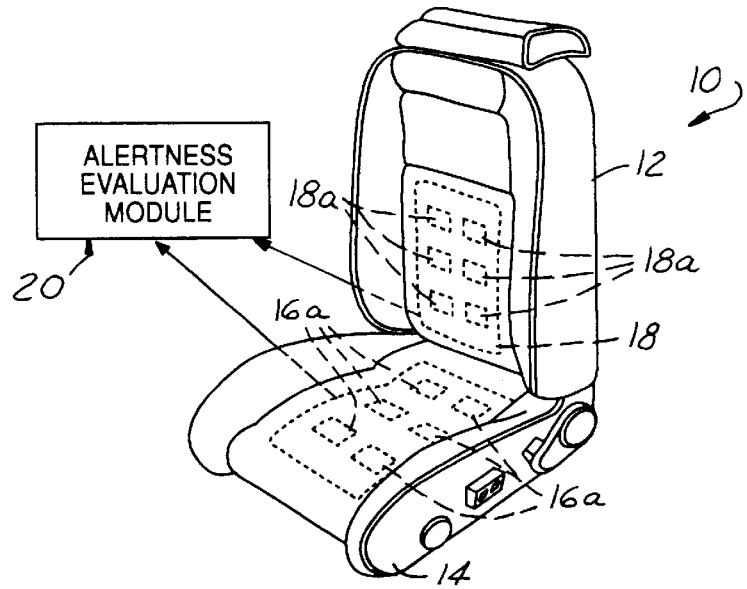
FIG. 1 is a perspective view of a vehicle seat equipped with a sensor array according to the invention.

Referring to FIG. 1, a seat 10 of an automotive vehicle is shown to generally comprise a seat back 12 and a seat bottom 14. A first pressure sensor array 16 is disposed in or on the surface of the seat bottom 14, and a second pressure sensor array 18 is disposed in or on the surface of the seat back 12. The sensor arrays 16,18 comprise a plurality of pressure sensing transducers or elements 16a,18a, each element detecting the pressure exerted at a discrete point on the seat 10 and producing electrical output signals indicating the sensed pressure. The output signals of the sensing elements 16a,18a combine to yield a pattern of pressure indicating the distribution of pressure over the portions of the seat surface area covered by the sensor arrays 16,18. The sensing elements 16a,18a may be any appropriate type of pressure sensing transducer known in the art, such as variable resistance sensors, capacitive sensors, or strain gages. A seat pressure sensor having a plurality of variable resistors located in a seat bottom is taught by U.S. Pat. No. 5,474,327, the disclosure of which is incorporated herein by reference. If desired, the two sensor arrays 16,18 may be combined into a single array covering portions of the seat back 12 and seat bottom 14.

The number and placement of the sensing elements 16a, 18a on the surface of the seat is such that the sensor arrays are able to detect a pressure pattern representative of the seated posture of the driver (not shown), and such that variations in the pressure pattern may be used to identify relatively subtle changes in the driver's seated posture. For example, the sensing elements 16a, 18a are preferably placed to detect whether the driver is seated in a relatively upright posture or is slouching or leaning forward. The sensor arrays 16,18 may also be able to detect left/right weight shifts, or combinations of forward/rear and left/right shifts.

The sensor arrays 16,18 are electrically connected with an alertness evaluation module 20, which is preferably a microprocessor-based device. The alertness evaluation module 20 receives pressure pattern data from the sensor arrays 16,18 at a predetermined sample rate, for example once per second, and monitors the pressure pattern data for indications of changes in the driver's seated posture. It has been found that certain changes in a driver's seated posture may indicate the onset of sleepiness or a decreased level of alertness. For example, the driver may sit relatively upright in the seat when fully alert, but gradually begin to slouch or slump forwardly when he/she becomes tired or sleepy. In other situations, the driver may exhibit an increase or decrease in the number and/or frequency of positional changes or "fidgeting" as he/she tires or becomes less alert. Either of these changes in seating posture can be detected by properly analyzing the output of one or both of the sensor arrays.

It is possible for pressure pattern data from a single sensor array located only in the seat bottom 14 or only in the seat back 12 to provide sufficient pressure pattern data to determine driver alertness in accordance with the present invention.

The alertness evaluation module 20 may also receive inputs from other vehicle systems that are pertinent to the alertness evaluation to be made. One example of such a vehicle system is the cruise control 22 (see FIG. 2), since the driver is typically likely to be less alert when not responsible for manual speed control of the vehicle or otherwise not using all of their motor skills. Another example is a yaw rate sensor 24 or steering input sensor (not shown) to provide information on whether the vehicle is being steered in a relatively stable path or is weaving.

The alertness evaluation module 20 preferably uses a neural network processing technique to determine the probable driver alertness level. A neural network, as is well known in the computing art, is an inter-connected assembly of simple processing elements, units, or nodes whose functionality is loosely based on the animal neuron. The processing ability of the network is stored in the inter-unit connection strengths, or weights, obtained by a process of adaption to, or learning from, a set of training patterns. This learning ability allows a neural network in the present invention to recognize a normal seated posture of a particular driver and when changes in the seated posture indicate the likelihood of a decreased level of alertness.

When the alertness evaluation module 20 has determined that the driver's alertness level has decreased below an acceptable level, it triggers one or more driver stimulating devices, such as an audible chime 26, a recorded or synthesized voice warning 28, a scent injector 30 that sprays an aroma into the passenger compartment, or a seat vibrator 32. Other appropriate stimulus providing devices are also within the scope of the invention.

Figure 2:
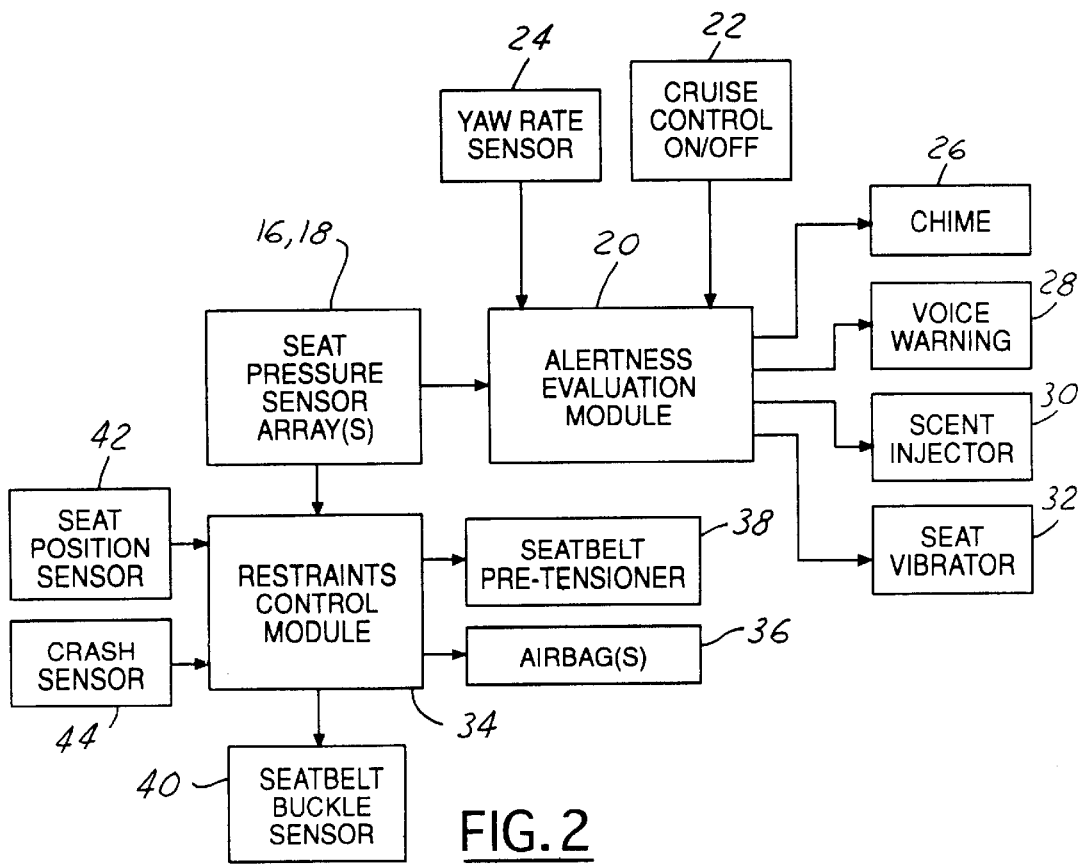
FIG. 2 is a schematic block diagram of an alertness monitoring system according to the present invention integrated with an occupant restraint control system.

As depicted in FIG. 2, the sensor arrays 16,18 may also provide inputs to a restraint control module (RCM) 34 of an occupant safety system. In such an application, the RCM 34 uses the output signals from the arrays 16,18 to detect and distinguish between large-statured and small-statured seat occupants, as well as child safety seats of various types. In accordance with known occupant restraint system concepts, the RCM 34 uses these and other inputs to make decisions regarding the deployment of airbags 36, seatbelt pretensioners 38, or other supplemental restraint system depending upon the physical characteristics of the seat occupants as detected by one or more sensors. Besides the seat pressure sensor arrays 16,18, the RCM 34 may also receive inputs from other sensors such as a seatbelt buckle sensor 40, a seat position sensor 42, and a crash sensor 44.

As is apparent from the above description, the invention system and method for reliably and accurately determine when the driver's level of alertness has degraded to the point where the driver may not be able to operate the vehicle safely. The use of a seat-mounted pressure sensor that may also provide occupant status information to an occupant restraint system controller results in cost savings since there is no need to use a dedicated alertness sensor.

Various other modifications and variations will no doubt occur to those skilled in the arts to which this invention pertains. Such variations and modifications, which generally rely on the teachings through which this disclosure has advanced the art, are properly considered within the scope of this invention. This disclosure should thus be considered illustrative, not limiting; the scope of the invention is instead defined by the following claims.

What is claimed is:

1. Apparatus for monitoring alertness of a driver seated in a seat of an automotive vehicle, the apparatus comprising:
 a sensor array disposed in the seat to sense a pattern of pressure exerted by the driver at a plurality of points distributed over a surface of the seat and produce output signals representing the pattern of pressure;
 an alertness evaluation module monitoring the output signals from the sensor array and determining a probable driver alertness level based upon changes in the pattern of pressure.

2. The apparatus of claim 1 wherein the alertness evaluation module determines the probable driver alertness level based at least in part upon a rate of driver positional changes.

3. The apparatus of claim 1 wherein the alertness evaluation module determines the probable driver alertness level based at least in part upon a tendency of the driver to slouch in the seat.

4. The apparatus of claim 1 wherein the alertness evaluation module utilizes a neural network processing technique to determine the probable driver alertness level.

5. The apparatus of claim 1 further comprising a driver stimulating device triggered when the alertness evaluation module determines that the driver's alertness has fallen below a minimum level.

6. The apparatus of claim 1 wherein the sensor array comprises a plurality sensing elements.

7. The apparatus of claim 6 wherein at least one of the sensing elements comprises a variable resistor.

8. The apparatus of claim 6 wherein at least one of the sensing elements comprises a strain gage measuring displacement of a seat component.

9. The apparatus of claim 1 wherein the sensor array is disposed in a back portion of the seat.

10. The apparatus of claim 1 wherein the sensor array is disposed in a bottom portion of the seat.

11. The apparatus of claim 1 wherein the sensor array provides inputs to a restraints control module for use in occupant restraint deployment decisions.

12. A method of monitoring alertness of a driver seated in a seat of an automotive vehicle, the method comprising the steps of:

measuring at a first time a first pattern of pressure exerted by the driver on a plurality of points distributed over a surface of the seat;

measuring at a second time a second pattern of pressure exerted by the driver on the plurality of points; and determining a probable driver alertness level based upon a comparison of the first and second patterns.

13. The method according to claim 12 wherein the step of determining the probable driver alertness level comprises monitoring a rate of driver positional changes.

14. The method according to claim 12 wherein the step of determining the probable driver alertness level comprises monitoring a tendency of the driver to slouch in the seat.

15. The method according to claim 12 wherein the step of determining the probable driver alertness level is performed by a alertness evaluation module utilizing a neural network processing technique.

16. The method according to claim 12 wherein the step of determining a probable driver alertness level comprises comparing at least one of the first and second patterns with pressure pattern data from previous occasions when the driver operated the vehicle.

17. A method of monitoring alertness of a driver seated in a seat of an automotive vehicle, the seat having an array of pressure sensors distributed over a surface of the seat for monitoring patterns of pressure exerted by the driver for use in occupant restraint deployment decisions made by a restraints control module, the method comprising the steps of:

monitoring a pattern of pressure exerted on a surface of the seat by the driver at a plurality of points on the surface; and determining a probable driver alertness level from the pattern and changes in the pattern over time.

18. The method according to claim 17 wherein the step of determining the probable driver alertness level comprises monitoring a rate of driver positional changes.

19. The method according to claim 17 wherein the step of determining the probable driver alertness level comprises monitoring a tendency of the driver to slouch in the seat.

20. The method according to claim 17 wherein the step of determining the probable driver alertness level is performed by a alertness evaluation module utilizing a neural network processing technique.

* * * * *